US009228909B1

(12) United States Patent
Rembisz et al.

(10) Patent No.: US 9,228,909 B1
(45) Date of Patent: Jan. 5, 2016

(54) METHODS AND SYSTEMS FOR SENSING TENSION IN A TIMING BELT

(71) Applicant: Google Inc., Mountain View, CA (US)

(72) Inventors: Justine Rembisz, San Francisco, CA (US); Aaron Edsinger, Mountain View, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/276,032

(22) Filed: May 13, 2014

(51) Int. Cl.
*G01L 3/02* (2006.01)
*G01L 3/08* (2006.01)
*G01P 3/44* (2006.01)
*F16C 41/00* (2006.01)

(52) U.S. Cl.
CPC ... *G01L 3/08* (2013.01); *G01L 3/02* (2013.01); *F16C 41/007* (2013.01); *G01P 3/443* (2013.01)

(58) Field of Classification Search
CPC .......... F16C 41/007; G01P 3/443; G01I 3/02
USPC ............................................. 73/862.31, 800
See application file for complete search history.

(56) References Cited

U.S. PATENT DOCUMENTS

| | | | |
|---|---|---|---|
| 5,019,017 A * | 5/1991 | Monch | F16H 61/6624 474/102 |
| 5,295,571 A * | 3/1994 | Van Den Bogaert et al. | 198/502.1 |
| 6,925,279 B2 * | 8/2005 | Kamoshita et al. | 399/303 |
| 2003/0111298 A1* | 6/2003 | Logan et al. | 187/391 |
| 2003/0168317 A1* | 9/2003 | Fromme et al. | 198/502.1 |

* cited by examiner

*Primary Examiner* — Max Noori
(74) *Attorney, Agent, or Firm* — McDonnell Boehnen Hulbert & Berghoff LLP

(57) ABSTRACT

In examples, methods and systems for sensing tension in a timing belt are provided. In one example, a transmission device is provided that comprises a timing belt transmission configured to cause rotation of an output hub, and the timing belt transmission includes a timing belt with markings. The transmission device also includes a detector for detecting the markings on the timing belt as the timing belt is placed under a tension due to a load at the output hub, and a distance between the markings on the timing belt changes as the timing belt is placed under the tension. The transmission device also includes one or more processors for determining output torque of the timing belt transmission based on the distance between the markings on the timing belt or based on a time between detected markings.

14 Claims, 6 Drawing Sheets

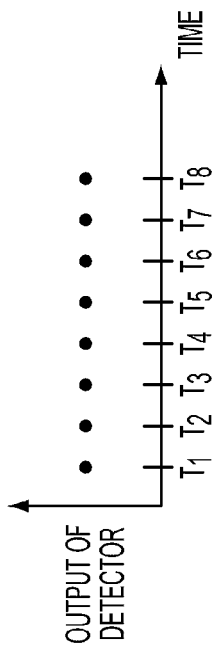
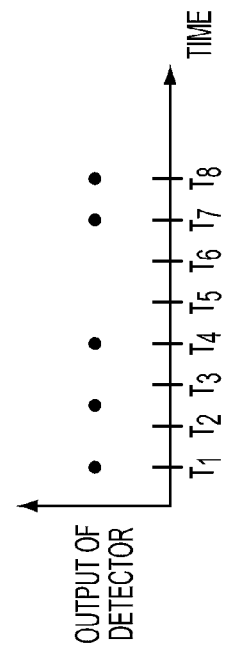
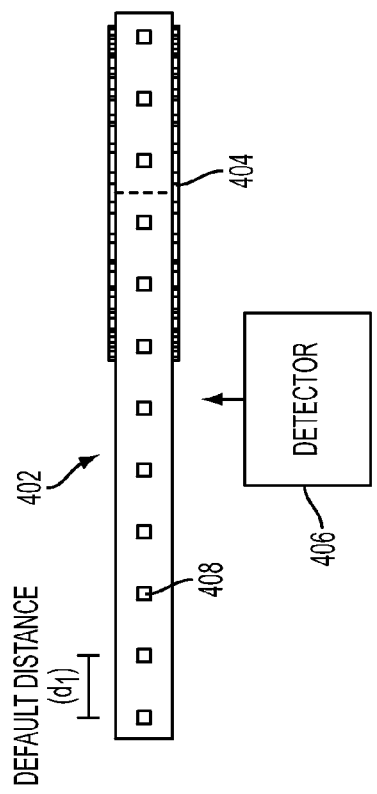
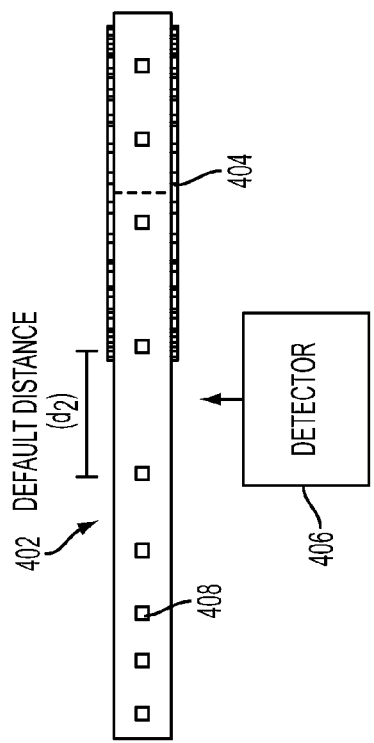
FIG. 4A
FIG. 4B
FIG. 5A
FIG. 5B

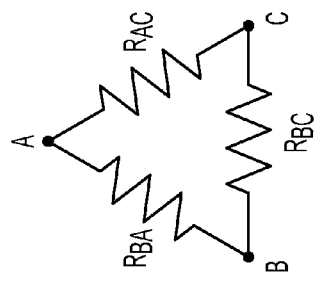
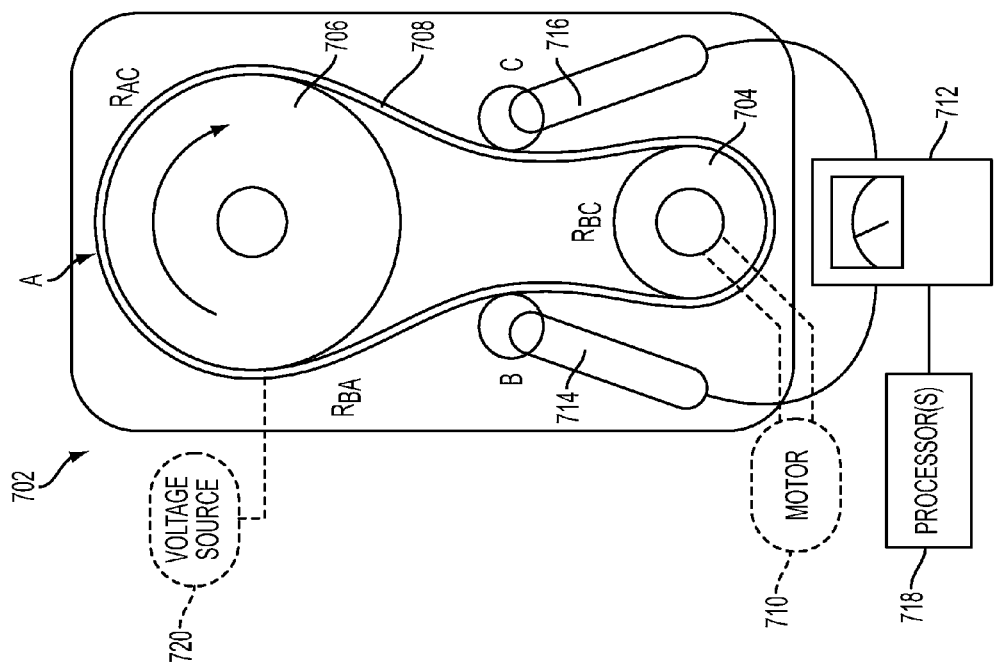

METHODS AND SYSTEMS FOR SENSING TENSION IN A TIMING BELT

BACKGROUND

Unless otherwise indicated herein, the materials described in this section are not prior art to the claims in this application and are not admitted to be prior art by inclusion in this section.

Electric motor actuators for robotic and automation systems often require a transmission (speed reducer) in order to operate within the speed-torque requirements of a specific application and of the motor. Commonly used systems include multi-stage gearboxes, timing belts, cables with capstans, harmonic drives, and cycloid gearboxes. These systems may have shortcomings, such as too inefficient, susceptible to overload damage, heavy, and require expensive precision manufacturing. Such systems are also often too expensive for consumer products when high performance is required.

As an example, harmonic drive systems can be used in high performance applications where low backlash and gear-ratios greater than 50:1 are required. The harmonic drive is proprietary, heavy, inefficient, susceptible to damage from shock load, and expensive for consumer application. As another example, cable drive systems can be lightweight and efficient; however, achieving useful transmission ratios may lead to complex multi-stage designs that require high preload forces, large cable bend radii, and challenging cable management. Often it is desired to integrate a torque sensor such as a strain gauge load cell at or near the output of the transmission in order to achieve closed loop torque control and to sense tension of the timing cable or belt. Practically, such as a case on a rotating output hub, integration of this sensor can prove challenging as the sensor wires typically rotate with the transmission output, and therefore, require cable management, adding complexity and increasing the number of failure points.

In other examples, a belt drive system can be implemented, and systems may be used to measure a tension of the belt drive during operation. Existing systems may utilize similar sensors (e.g., strain gauges) to measure the tension, and such sensors may add to complexity and cost of the belt drive system.

SUMMARY

In one example, a transmission device is provided that comprises a timing belt transmission configured to cause rotation of an output hub, and the timing belt transmission includes a timing belt with markings. The transmission device also includes a detector for detecting the markings on the timing belt as the timing belt is placed under a tension due to a load at the output hub, and a distance between the markings on the timing belt changes as the timing belt is placed under the tension. The transmission device also includes one or more processors for determining output torque of the timing belt transmission based on the distance between the markings on the timing belt or based on a time between detected markings.

In another example, a method is provided that comprises rotating an output hub using a timing belt transmission, and the timing belt transmission includes a timing belt with markings. The method also includes detecting the markings on the timing belt as the timing belt is placed under a tension due to a load at the output hub, and a distance between the markings on the timing belt changes as the timing belt is placed under the tension. The method further includes determining output torque of the timing belt transmission based on the distance between the markings on the timing belt or based on a time between detected markings.

In still another example, a transmission device is provided that comprises a timing belt transmission configured to cause rotation of an output hub, and the timing belt transmission includes a timing belt. The transmission device also includes a voltage source coupled to the timing belt to apply a voltage to the timing belt, and a detector for detecting a resistance of the timing belt as the timing belt is placed under a tension and stretches due to a load at the output hub. The transmission device further includes one or more processors for determining output torque of the timing belt transmission based on the resistance of the timing belt.

In another example, a system is provided that comprises a means for rotating an output hub using a timing belt transmission, and the timing belt transmission includes a timing belt with markings. The system also includes a means for detecting the markings on the timing belt as the timing belt is placed under a tension due to a load at the output hub, and a distance between the markings on the timing belt changes as the timing belt is placed under the tension. The system further includes a means for determining output torque of the timing belt transmission based on the distance between the markings on the timing belt or based on a time between detected markings.

In still other examples, methods and computer program products including instructions executable by a device or by one or more processors to perform functions of the methods are provided. The methods may be executable for operating a transmission device, for example.

These as well as other aspects, advantages, and alternatives, will become apparent to those of ordinary skill in the art by reading the following detailed description, with reference where appropriate to the accompanying figures.

BRIEF DESCRIPTION OF THE FIGURES

FIG. 3A illustrates a top view of the example pulley and belt, FIG. 3B illustrates a side view of the example pulley and belt, FIG. 3C illustrates a top perspective view of the example pulley and belt, and FIG. 3D illustrates a bottom perspective view of the example pulley and belt.

FIGS. 4A-4B illustrate another example belt and pulley arrangement.

FIGS. 5A-5B show example timing diagrams for outputs from a detector, such as the detector in FIG. 4.

FIG. 7A illustrates another example transmission device.

FIG. 7B illustrates a conceptual resistor diagram of the belt in FIG. 7A.

DETAILED DESCRIPTION

The following detailed description describes various features and functions of the disclosed systems and methods with reference to the accompanying figures. In the figures, similar symbols identify similar components, unless context dictates otherwise. The illustrative system and method embodiments described herein are not meant to be limiting. It may be readily understood that certain aspects of the disclosed systems and methods can be arranged and combined in a wide variety of different configurations, all of which are contemplated herein.

Within examples, a robotic manipulator may include a torque controlled actuator that has an electric motor attached to a transmission, and the transmission may include an N-stage belt transmission arranged in a serial fashion that connects rotation of the motor to rotation of an output. Each stage of the transmission may include a timing belt, a belt tensioning mechanism, and a tension measuring system.

Within examples herein, the timing belt (of stages) may include markings on the belt that are spaced (e.g., equally spaced apart). As the belt is placed under a tension (due to an applied load to the robotic manipulator), the belt may be stretched and a distance between the markings may be increased. The distance between markings on the belt can be measured or determined, and correlated to a tension that the belt is experiencing based on stretching of the belt (e.g., as belt stretches, determine distance between marks for tension).

In other examples, the timing belt may have resistive properties that change as the belt stretches or is placed under a tension, and the change in resistance can be determined and correlated to a tension that the belt is experiencing. A voltage can be applied to the belt, and resistance changes can be determined across two contact points (e.g., acting as electrodes) on the belt.

In still other examples, the timing belt may comprise a steel type belt, and a magneto-elastic effect of properties in the steel belt can be measured and correlated with changes in tension.

Thus, within examples, the timing belt may include properties that change based on applied tension to the belt, and the change(s) in the properties can be detected and correlated with amounts of tension being experienced. The properties may include physical markings on the belt, or material changes of the belt (e.g., resistive change). The amounts of tension are useful to determine torque applied, which can be used for motor control, for example.

Figure 1:
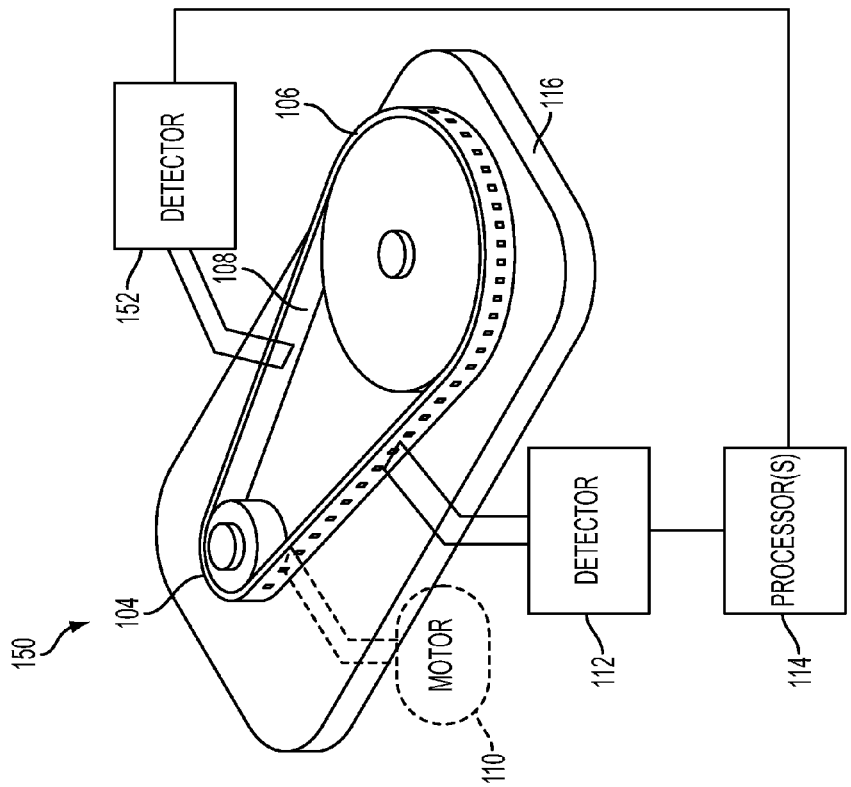
FIG. 1 illustrates an example transmission device including a timing belt transmission.

Referring now to the figures, FIG. 1 illustrates an example transmission device including a timing belt transmission 102 with an input hub 104 and an output hub 106, and a timing belt 108 wrapped around the input hub 104 and the output hub 106 in a loop. The input hub 104 and the output hub 106 may comprise pulleys mounted on rolling bearings, for example. A motor 110 is provided coupled to the input hub 104 to cause rotation of the input hub 104. The timing belt transmission 102 is then configured to cause rotation of the output hub 106 due to movement of the timing belt 108 around the output hub 106. Thus, due to the configuration of the timing belt 108 wrapping around the input hub 104 and the output hub 106 in a loop, rotation of the input hub 104 causes rotation of the output hub 106.

The timing belt 108 includes markings on a surface of the timing belt 108. The transmission device also includes a detector 112 for detecting the markings on the timing belt 108. For example, a load (not shown) may be applied at the output hub 104 that places a tension on the timing belt 108. The detector 112 may detect the markings on the timing belt 108 as the timing belt 108 is placed under the tension due to the load, and a distance between the markings on the timing belt 108 may change as the timing belt 108 is placed under the tension. The detector 112 is positioned between the input hub 104 and the output hub 106 for detecting the markings on the timing belt 108 as the timing belt 108 moves due to rotation of the input hub 104 and the output hub 106.

The transmission device further includes one or more processors 114 for determining output torque of the timing belt transmission based on the distance between the markings on the timing belt 108 or based on a time between detected markings.

Components of the transmission device may be provided or mounted on a frame 116. In FIG. 1, a single timing belt stage for the transmission device is shown. However, in other examples, more than one timing belt stage may be provided and coupled in serial on the frame 116 for further speed reduction of the motor 110. Thus, the design may be implemented as an N-stage system including 1-N timing belt stages. Each timing belt stage provides a reduction of motor input speed while it increases torque output.

As shown in FIG. 1, the motor 110 is positioned on one side of the frame 116, and the timing belt stage is positioned on the other side of the frame 116.

The example transmission device thus includes a motor driven belt system to drive the output hub 106 that uses the detector 112 to determine information related to belt tension, from which torque of the device can be deduced (i.e., to convert units of strain from output of strain gauge to units of torque).

The timing belt 108 may exhibit zero backlash, which enables precise applications. The timing belt 108 also exhibits transmission compliance, which makes the device non-stiff and therefore safer for human contact when employed as a joint in a robotic manipulator, for example. Sensing of belt tension of the output stage enables direct measurement and control of the joint torque, and cancellation of transmission friction by closing a servo control loop around a force sensor.

Figure 2:
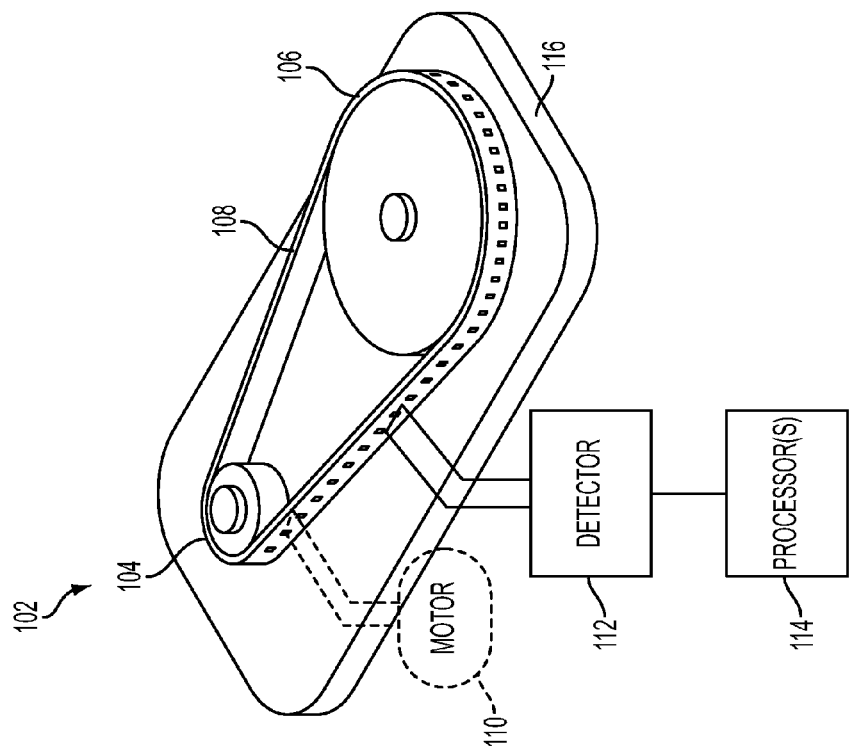
FIG. 2 illustrates another example transmission device including a timing belt transmission.

FIG. 2 illustrates an example transmission device including a timing belt transmission 150 with components similar to the timing belt transmission 102 in FIG. 1, and also including a second detector 152. The detector 152 is shown to detect markings on the timing belt 108 on a side opposite the detector 112.

The detectors 112 and 152 may be the same or similar detectors and may include an optical encoder to detect the markings on the timing belt 108. The detectors 112 and 152 may further include a light source to shine onto the timing belt 108, and a photo-detector to detect occurrence of the markings on the timing belt 108 based on reflected light. In other examples, the detectors 112 and 152 may include a camera to capture images of the timing belt 108 for processing to identify markings or property changes of the timing belt 108. In still other examples, the detectors 112 and/or 152 may include a quadrature sensor to both detect the markings and a direction of travel of the timing belt 108.

In other examples, where the markings on the timing belt 108 include a groove, a bump, or a difference in surface texture, the detectors 112 and 152 may touch or contact the timing belt 108 to detect the markings, and may cause a counter to increment upon each detected marking.

The processor(s) 114 are configured to receive outputs from the detector 112 (or from both detectors 112 and 152) indicating detection of the markings, and correlate the detections to a tension on the timing belt 108. In one example, the processor 114 may determine a time between detected markings based on the outputs from the detectors 112 and 152 (which may be time-stamped, or the processor 114 may time stamp upon receipt of the outputs), and determine a speed of rotation of the output hub 106 based on speed of the motor 110 (e.g., the processor 114 may receive the speed input to the motor 110). The processor 114 may then determine the distance between the markings based on the speed of rotation of the output hub 106 and the time between detected markings, for example. The distance between the markings may be indicative of how much the timing belt 108 has stretched when compared to default distances (e.g., due to application of the load at the output hub 106), which maps to a tension in the timing belt 108. Rotation of the input hub 104 at certain rates may also cause some stretching of the timing belt 108 as well.

In some examples, the distance between the markings on the timing belt 108 increases as the timing belt 108 stretches due to the tension. Thus, the processor 114 determines an increase in output torque of the transmission device 102 based on the distance between the markings on the timing belt 108 increasing, and a decrease in output torque of the transmission device based on the distance between the markings on the timing belt 108 decreasing. In other examples, a time at which markings are detected may increase (due to the belt stretching). Thus, the processor determines an increase in output torque of the transmission device 102 based on the time between detected markings on the timing belt 108 increasing, and a decrease in output torque of the transmission device based on the time between detected markings on the timing belt 108 decreasing.

Figure 3B:
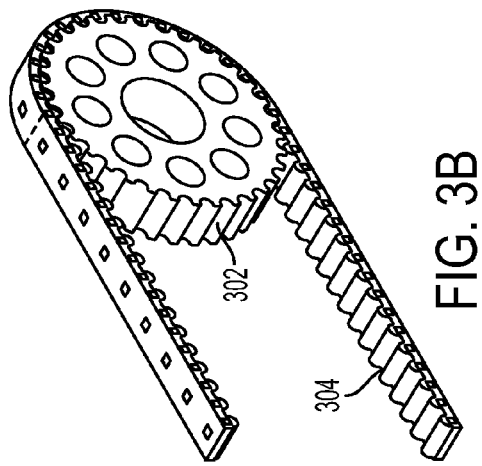
FIGS. 3A-3D illustrate an example timing pulley and timing belt.
Figure 3D:
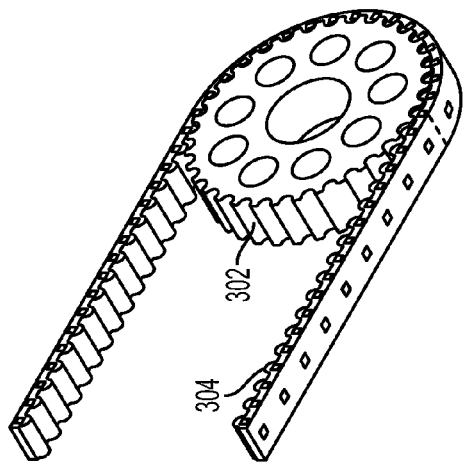
Figure 3A:
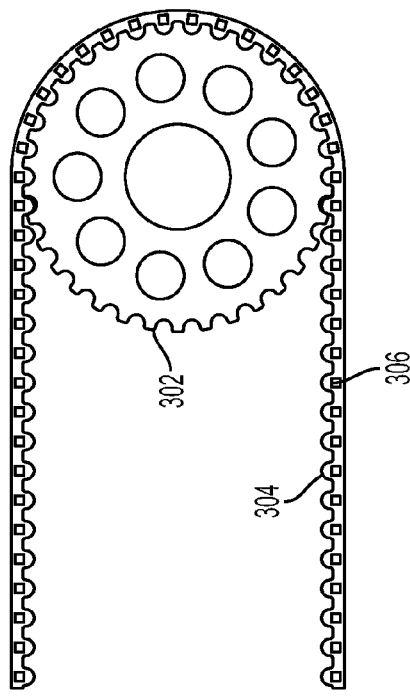
Figure 3C:
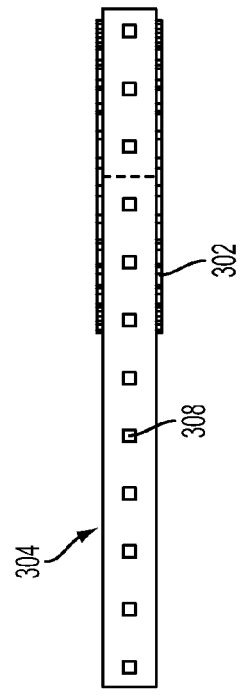

FIGS. 3A-3D illustrate an example timing pulley 302 and timing belt 304. FIG. 3A illustrates a top view of the example pulley 302 and belt 304, FIG. 3B illustrates a side view of the example pulley 302 and belt 304, FIG. 3C illustrates a top perspective view of the example pulley 302 and belt 304, and FIG. 3D illustrates a bottom perspective view of the example pulley 302 and belt 304.

In FIGS. 3A-3D the pulley 302 includes teeth, and the belt 304 is a toothed belt that interlocks to the teeth of the pulley 302. The pulley 304 may be any of the pulleys in FIGS. 1-2 including the input hub and/or output hub.

The belt 304 has a specific tooth profile and enables accurate positioning on the pulley 302 along with an ability to efficiently transfer high loads, for example. For example, the tooth profile of the belt 304 matches the tooth profile of the pulley 302 to match together for zero backlash.

The belt 304 includes markings, such as marking 306 in FIG. 3A or marking 308 in FIG. 3B. The marking 306 in FIG. 3A is shown in a side surface of the belt 304 and lined up with teeth of the belt 304, for example. The marking 308 in FIG. 3B is shown on a top surface of the belt 304 or a surface of the belt 304 opposite the teeth, such as an exterior surface. The markings on the belt 304 may be approximately equally spaced apart (e.g., or within manufacturing tolerances) on the belt 304, and provided along a full length of the belt 304, or provided along a substantial portion of the length of the belt 304.

The markings may be any number of markings, such as laser markings shown ticks along the belt 304, a marking of any color opposite a color of the belt, or any other physical marking on the belt 304. In other examples, the marking may include surface texture markings, such as an indenture, a groove, a bump, or change in shape of the belt 304 along a center region of the belt.

FIGS. 4A-4B illustrate another example belt and pulley arrangement. In FIG. 4A, a belt 402 is provided around a pulley 404, and a detector 406 is positioned adjacent the belt 402 to detect markings 408 on the belt 402. Although the markings are shown on a flat exterior surface of the belt 402 and the detector 406 adjacent the belt 402, the markings may alternatively or additionally be on a top surface of the belt 402 (e.g., as shown in FIG. 3A on the belt 304), and the detector 406 can be configured to detect the markings on the top and/or on the side of the belt 402 due to placement of the detector 406 (or due to placement of portions of the detector 406), for example. In the example shown in FIG. 4A, conceptually no load is applied to the belt 402. The markings are a default distance ($d_1$) apart based on absence of the load at the pulley 404.

In FIG. 4B, an example is shown where a load is applied to the belt 402, and thus, the belt is placed under tension. The belt 402 may stretch causing a distance between markings to increase to distance $d_2$. The detector 406 (or a processor) may determine the default distance $d_1$ between the markings on the belt 402, and determine a difference between the default distance $d_1$ and the distance $d_2$ between the markings on the belt 402 as the belt 402 is placed under the tension. Output torque may be determined based on the difference between the default distance $d_1$ and the distance $d_2$ between the markings on the belt 402 as the belt 402 is placed under the tension. As the difference in distance increases, the output torque may be determined to be increasing as well, causing stretching of the belt 402.

FIGS. 5A-5B show example timing diagrams for outputs from a detector, such as the detector 406 in FIG. 4. In FIG. 5A, the example timing diagram shows outputs from the detector 406 indicating when markings are detected on the belt 402. In this example, the markings are detected at approximately equally spaced time intervals, and it may be determined that no load (or a substantially small load) is being applied to the belt 402 resulting in no tension (or substantially small tension) being experienced by the belt 402. This is because the detector 402 outputs indications of detected markings at equally spaced time intervals indicating that the belt 402 is not being stretched.

In FIG. 5B, the example timing diagram shows outputs from the detector 406 at irregularly spaced time intervals indicating that the belt 402 is being stretched, which is due to an experienced tension from an applied load, for example.

The timing of detected markings may be correlated to a tension being experienced by the belt 402 or an output torque as well, based on a speed of rotation of the belt 402 and the pulley 404. For example, as the time between detected markings increases, the tension being experienced by the belt 402 increases as well, since the time between detected markings may be correlated with stretching of the belt due to increased tension.

Figure 6:
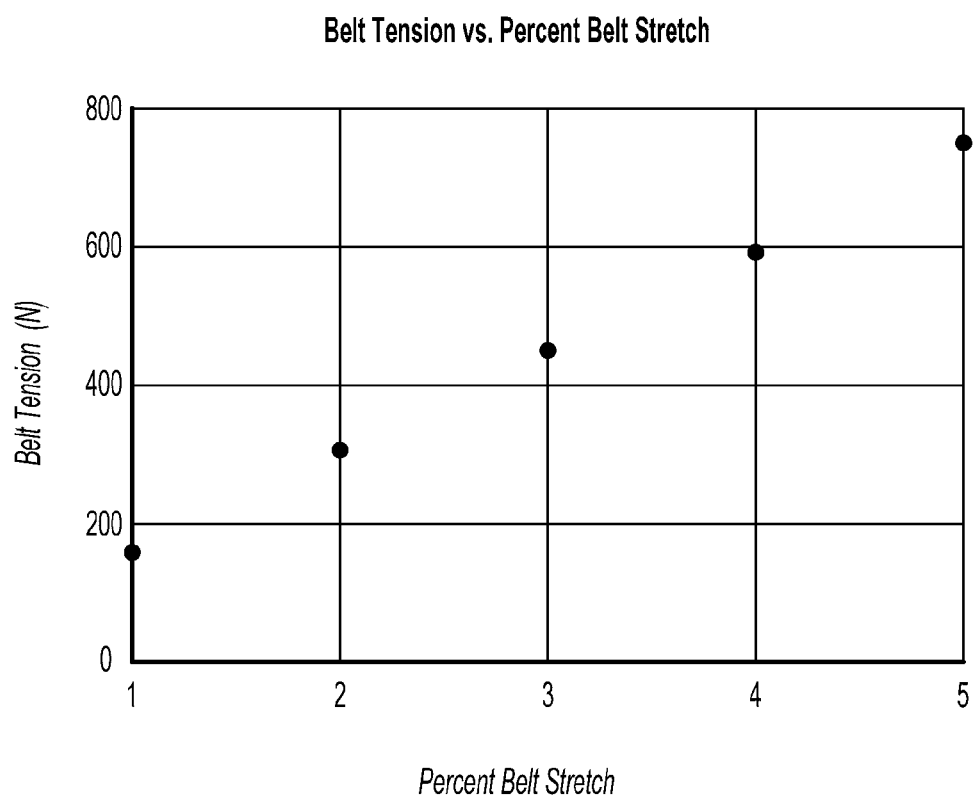
FIG. 6 is a graph illustrating example belt tension (N) vs. percent belt stretch.

FIG. 6 is a graph illustrating example belt tension (N) vs. percent belt stretch. In the example shown, a belt tension of about 180 N may be experienced by an example timing belt which results in approximately 1% stretching of the timing belt. As shown in FIG. 6, as the tension being experienced by the example timing belt increases, the percentage that the timing belt stretches also increases, such as up to about 5% stretch when the tension being experienced approaches 800 N.

Examples amounts of belt stretching (or percentages of belt stretching) due to tension being experienced may be based on many factors, including a type or material of the timing belt. For timing belts comprising rigid materials, less stretching may occur for a given tension as compared to timing belts comprising more flexible materials (e.g., rubber) for the same amount of tension.

FIG. 7A illustrates another example transmission device including a timing belt transmission 702 with an input hub 704 and an output hub 706, and a timing belt 708 wrapped around the input hub 704 and the output hub 706 in a loop. The input hub 704 and the output hub 706 may comprise pulleys mounted on rolling bearings, for example. A motor 710 is provided coupled to the input hub 704 to cause rotation of the input hub 704. The timing belt transmission 702 is then configured to cause rotation of the output hub 706 due to movement of the timing belt 708 around the output hub 706, similar to the transmission device in FIG. 1, for example.

The timing belt transmission 702 also includes a detector 712 that may include two probes 714 and 716 to contact the belt 708. The two probes 714 and 716 may detect markings on the belt 708, in an example in which the markings include surface textures on the belt (e.g., indentations, grooves, bumps, etc.). A processor 718 may receive outputs from the detector 712 to determine tension experienced by the belt 708.

In another example, the timing belt transmission 702 may include a voltage source 720 that couples to the output hub 706. The belt 708 may be of a conductive material, or may include conductive properties, and as the belt 708 contacts the output hub 706, a voltage is applied to the belt 708. For instance, the belt 708 may include a woven conductor or other electrical conductive material. In other examples, voltage may be applied to the belt 708 in other manners such as through an additional probe (not shown) contacting the belt 708.

The detector 712 may detect a resistance of the timing belt 708 when no load is present at the output hub, and then detect a resistance of the timing belt 708 as the timing belt 708 is placed under a tension and stretches due to the presence of a load at the output hub 706, for example. The processor 718 may be coupled to the detector 712 and may determine output torque of the timing belt transmission 702 based on the resistance of the timing belt 708, or based on a change in the resistance of the timing belt 708.

In this example, the detector 712 contacts the timing belt 708 across two contact points and detects the resistance across the two contact points. In FIG. 7A, the two contact points are labeled B and C, for example.

FIG. 7B illustrates a conceptual resistor diagram of the belt 708 in FIG. 7A, in which the belt 708 may be modeled as three resistors in series. The resistors are modeled across three positions of the belt 708 labeled A, B, and C. The three resistors are labeled $R_{BA}$, $R_{AC}$, and $R_{BC}$. In this example, a default resistance of the belt 708 may be known or default resistances of the modeled resistors $R_{BA}$, $R_{AC}$, and $R_{BC}$ may be known, and the detector 712 is configured to measure the resistance of the portion of the belt 708 modeled as resistor $R_{BC}$.

The processor 718 may thus determine the output torque of the timing belt transmission based on a change in the resistance of the timing belt 708 as the timing belt 708 is placed under the tension.

Within examples, the timing belt 708 may comprise materials that change resistance based on application of a load, or pressure applied to the timing belt 708. In one example, the timing belt 708 may comprise a force-sensing resistor material that changes resistance when a force or pressure is applied. Force-sensing resistors include a conductive polymer that changes resistance in a predictable manner following application of force to its surface. The timing belt 708 may include a polymer sheet or ink that can be applied by screen printing, and a sensing film includes both electrically conducting and non-conducting particles suspended in matrix. Applying a force to the surface of the sensing film causes particles to touch the conducting electrodes, changing the resistance of the film. A default resistance of the timing belt 708 can be determined, when no load is applied, and resistances of the timing belt 708 under various loads can be measured to calibrate a resistance of the timing belt 708 to output loads. Strain gauges or load cells may also be used during calibration to measure or detect tension of the timing belt 708 comprising such force-sensing resistive material to correlate tensions to detected resistance changes for certain output loads.

Such example calibration processes can be performed for a number of different materials used in timing belts to map resistance changes to tensions being experienced based on various output loads, for example. In other examples, calibration processes can be performed for a number of different materials used in timing belts to map resistance changes to output torques being experienced based on various output loads, for example.

In further examples, multiple detectors may be provided in the timing belt transmission 702. For example, the detector 712 may measure the resistance of a portion of the belt 708 labeled $R_{BC}$, another detector (not shown) may measure the resistance of a portion of the belt 708 labeled $R_{BA}$, and still another detector (not shown) may measure the resistance of a portion of the belt 708 labeled $R_{AC}$. One or more of these resistances may be measured to determine resistance changes, as compared to known or default resistances, and correlate the measured resistance or resistance change to the tension experienced by the belt 708. In this example, one detector may be positioned between the input hub 704 and the output hub 706 on a first side of the loop of the timing belt 708 to measure the resistance $R_{BA}$, and another detector may be positioned between the input hub 704 and the output hub 706 on a second or opposite side of the loop of the timing belt 708 to measure the resistance $R_{AC}$. The processor 718 may determine the output torque of the timing belt transmission based on a difference between respective resistances of the timing belt 708 output by the detectors.

Figure 8:
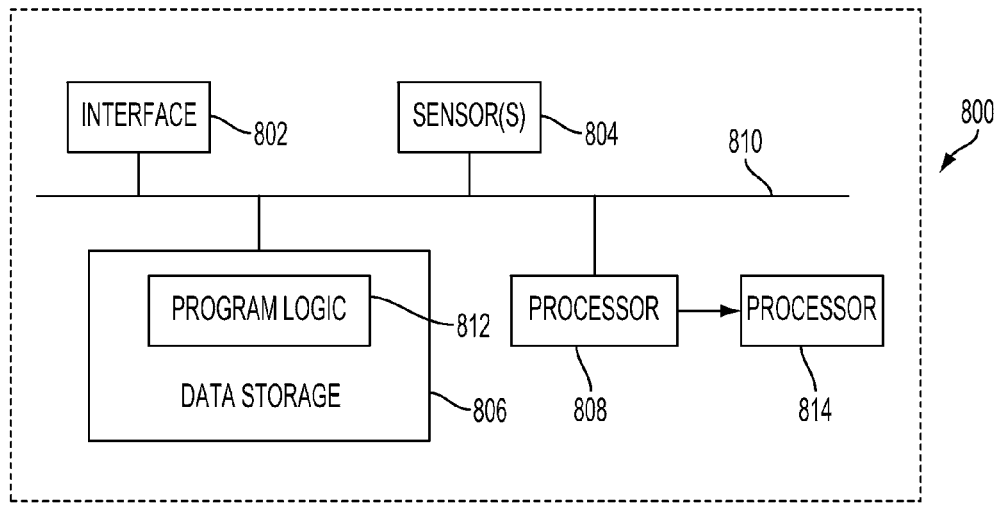
FIG. 8 illustrates a schematic drawing of an example computing device.

FIG. 8 illustrates a schematic drawing of an example computing device 800. The computing device 800 may represent components of transmission devices described herein (such as the detectors and processors), for example. In some examples, some components illustrated in FIG. 8 may be distributed across multiple computing devices. However, for the sake of example, the components are shown and described as part of one example device 800. The device 800 may be or include a mobile device, desktop computer, tablet computer, or similar device that may be configured to perform the functions described herein.

The device 800 may include an interface 802, sensor(s) 804, data storage 806, and a processor 808. Components illustrated in FIG. 8 may be linked together by a communication link 810. The communication link 810 is illustrated as a wired connection; however, wireless connections may also be used. The device 800 may also include hardware to enable communication within the device 800 and between the client device 800 and another computing device (not shown), such as a server entity. The hardware may include transmitters, receivers, and antennas, for example.

The interface 802 may be configured to allow the device 800 to communicate with another computing device (not shown), such as a server. Thus, the interface 802 may be configured to receive input data from one or more computing devices, and may also be configured to send output data to the one or more computing devices. The interface 802 may also be configured to receive input from and provide output to a torque controlled actuator or modular link of a robot arm, for example. The interface 802 may include a receiver and transmitter to receive and send data. In other examples, the interface 802 may also include a user-interface, such as a keyboard, microphone, touchscreen, etc., to receive inputs as well.

The sensor 804 may include one or more sensors, or may represent one or more sensors included within the device 800. Example sensors include an accelerometer, gyroscope, pedometer, light sensors, microphone, camera, multi-meter, contact rollers, or other location and/or context-aware sensors that may collect data of the timing belt (e.g., motion of timing belt pulleys or idlers) and provide the data to the data storage 806 or processor 808.

The processor 808 may be configured to receive data from the interface 802, sensor 804, and data storage 806. The data storage 806 may store program logic 812 that can be accessed and executed by the processor 808 to perform functions executable to determine instructions for operation of the differential pulley actuator. Example functions include determination of tension experienced by the belt or output torque of the system, and optionally angular displacements of output pulleys based on a control loop or other feedback mechanism to determine desired output torques. Any functions described herein, or other example functions for the transmission device may be performed by the device 800 or one or more processors 808 of the device via execution of instructions stored on the data storage 806 or otherwise received.

The device 800 is illustrated to include an additional processor 914. The processor 814 may be configured to control other aspects of the device 800 including displays or outputs of the device 800 (e.g., the processor 814 may be a GPU). Example methods described herein may be performed individually by components of the device 800, or in combination by one or all of the components of the device 800. In one instance, portions of the device 800 may process data and provide an output internally in the device 800 to the processor 814, for example. In other instances, portions of the device 800 may process data and provide outputs externally to other computing devices.

Within some examples herein, operations may be described as methods for performing functions, and methods may be embodied on a computer program product (e.g., a tangible computer readable storage medium or non-transitory computer readable medium) that includes instructions executable to perform the functions.

Figure 9:
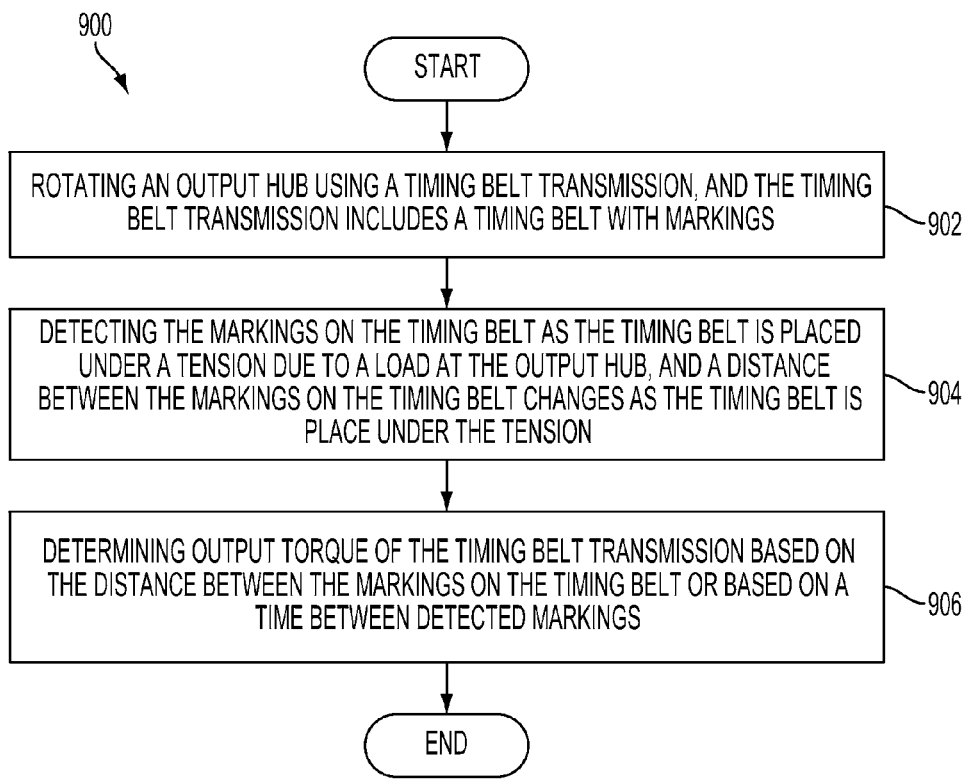
FIG. 9 is a flowchart illustrating an example method for operating a transmission device.

FIG. 9 is a flowchart illustrating an example method 900 for operating a transmission device. The method 900 may be embodied as computer executable instructions stored on non-transitory media, for example. At block 902, the method 900 includes rotating an output hub using a timing belt transmission, and the timing belt transmission includes a timing belt with markings. At block 904, the method 900 includes detecting the markings on the timing belt as the timing belt is placed under a tension due to a load at the output hub, and a distance between the markings on the timing belt changes as the timing belt is placed under the tension. At block 906, the method 900 includes determining output torque of the timing belt transmission based on the distance between the markings on the timing belt or based on a time between detected markings.

Within examples, the method 900 also includes determining, by one or more processors, a default distance between the markings on the timing belt, determining, by the one or more processors, a difference between the default distance and the distance between the markings on the timing belt changes as the timing belt is placed under the tension, and determining, by the one or more processors, the output torque based on the difference between the default distance and the distance between the markings on the timing belt changes as the timing belt is placed under the tension. In still further examples, the method 900 includes receiving outputs from the detector indicating detection of the markings, determining the time between detected markings, determining a speed of rotation of the output hub, and determining, by one or more processors, the distance between the markings based on the speed of rotation of the output hub and the time between detected markings.

The transmission device described in FIGS. 1-9 above may be used in many implementations. Example implementations include within a modular robot link or actuator system.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. A transmission device comprising:
 a timing belt transmission configured to cause rotation of an output hub, wherein the timing belt transmission includes a timing belt with markings;
 a motor connected to a pulley of an input hub, and configured to cause rotation of the input hub, wherein the timing belt wraps around the input hub and the output hub in a loop, such that rotation of the input hub causes rotation of the output hub;
 a detector for detecting the markings on the timing belt as the timing belt is placed under a tension due to a load at the output hub, wherein a distance between the markings on the timing belt changes as the timing belt is placed under the tension, wherein the detector is positioned between the input hub and the output hub for detecting the markings on the timing belt as the timing belt moves due to rotation of the input hub and the output hub; and
 one or more processors for determining output torque of the timing belt transmission based on the distance between the markings on the timing belt or based on a time between detected markings.

2. The transmission device of claim 1, wherein a distance between the markings on the timing belt increases as the timing belt stretches due to the tension.

3. The transmission device of claim 1, wherein the one or more processors determine an increase in output torque of the timing belt transmission based on the distance between the markings on the timing belt increasing, and the one or more processors determine a decrease in output torque of the timing belt transmission based on the distance between the markings on the timing belt decreasing.

4. The transmission device of claim 1, wherein the one or more processors determine an increase in output torque of the timing belt transmission based on the time between detected markings on the timing belt increasing, and the one or more processors determine a decrease in output torque of the timing belt transmission based on the time between detected markings on the timing belt decreasing.

5. The transmission device of claim 1, wherein the one or more processors determine a default distance between the markings on the timing belt, and determine a difference between the default distance and the distance between the markings on the timing belt changes as the timing belt is placed under the tension.

6. The transmission device of claim 5, wherein the default distance is determined based on absence of the load at the output hub.

7. The transmission device of claim 5, wherein the one or more processors determine the output torque based on the difference between the default distance and the distance between the markings on the timing belt changes as the timing belt is placed under the tension.

8. The transmission device of claim 1, wherein the markings on the timing belt are approximately equally spaced apart on the timing belt, and provided along a length of the timing belt.

9. The transmission device of claim 1, wherein the detector comprises an optical encoder to detect the markings on the timing belt.

10. The transmission device of claim 1, wherein the one or more processors are configured to:
   receive outputs from the detector indicating detection of the markings;
   determine the time between detected markings;
   determine a speed of rotation of the output hub; and
   determine the distance between the markings based on the speed of rotation of the output hub and the time between detected markings.

11. The transmission device of claim 1, wherein the timing belt includes properties that change as the timing belt is placed under the tension due to the load at the output hub, and
   wherein the one or more processors are configured to determine changes in the properties of the timing belt and correlate the changes with amounts of tension being experienced by the timing belt.

12. A method comprising:
   rotating an output hub using a timing belt transmission, wherein the timing belt transmission includes a timing belt with markings and a motor connected to a pulley of an input hub, wherein the timing belt wraps around the input hub and the output hub in a loop, such that rotation of the input hub causes rotation of the output hub;
   detecting, by a detector, the markings on the timing belt as the timing belt is placed under a tension due to a load at the output hub, wherein a distance between the markings on the timing belt changes as the timing belt is placed under the tension, wherein the detector is positioned between the input hub and the output hub for detecting the markings on the timing belt as the timing belt moves due to rotation of the input hub and the output hub; and
   determining output torque of the timing belt transmission based on the distance between the markings on the timing belt or based on a time between detected markings.

13. The method of claim 12, further comprising:
   determining, by one or more processors, a default distance between the markings on the timing belt;
   determining, by the one or more processors, a difference between the default distance and the distance between the markings on the timing belt changes as the timing belt is placed under the tension; and
   determining, by the one or more processors, the output torque based on the difference between the default distance and the distance between the markings on the timing belt changes as the timing belt is placed under the tension.

14. The method of claim 12, further comprising:
   receiving outputs from the detector indicating detection of the markings;
   determining the time between detected markings;
   determining a speed of rotation of the output hub; and
   determining, by one or more processors, the distance between the markings based on the speed of rotation of the output hub and the time between detected markings.

* * * * *